(12) United States Patent
Dalene et al.

(10) Patent No.: US 10,321,862 B2
(45) Date of Patent: Jun. 18, 2019

(54) NIRS SENSOR ASSEMBLY INCLUDING ELECTRICALLY CONDUCTIVE AND OPTICALLY TRANSPARENT EMI SHIELDING

(75) Inventors: Matthew Dalene, Clinton, CT (US); Karen Duffy, Orange, CT (US)

(73) Assignee: CAS Medical Systems, Inc., Branford, CT (US)

( * ) Notice: Subject to any disclaimer, the term of this patent is extended or adjusted under 35 U.S.C. 154(b) by 288 days.

(21) Appl. No.: 13/985,232

(22) PCT Filed: Feb. 13, 2012

(86) PCT No.: PCT/US2012/024889
§ 371 (c)(1),
(2), (4) Date: Oct. 25, 2013

(87) PCT Pub. No.: WO2012/109661
PCT Pub. Date: Aug. 16, 2012

(65) Prior Publication Data
US 2014/0051956 A1    Feb. 20, 2014

Related U.S. Application Data

(60) Provisional application No. 61/442,273, filed on Feb. 13, 2011, provisional application No. 61/546,821, filed on Oct. 13, 2011.

(51) Int. Cl.
*A61B 5/1455* (2006.01)
*A61B 5/00* (2006.01)

(52) U.S. Cl.
CPC ........ *A61B 5/14552* (2013.01); *A61B 5/0075* (2013.01); *A61B 5/14553* (2013.01); *A61B 2562/182* (2013.01)

(58) Field of Classification Search
None
See application file for complete search history.

(56) References Cited

U.S. PATENT DOCUMENTS

| 5,217,013 A * | 6/1993 | Lewis ................ A61B 5/0091 356/41 |
| 6,456,862 B2 | 9/2002 | Benni |
| 7,047,054 B2 | 5/2006 | Benni |
| 2001/0024549 A1 | 9/2001 | Takahashi et al. |
| 2002/0016536 A1 | 2/2002 | Benni |

(Continued)

OTHER PUBLICATIONS

Chinese office action for CN2012800181468 dated Jul. 30, 2015.
EP search report for EP12744543.5 dated Sep. 22, 2016.

*Primary Examiner* — Eric F Winakur
*Assistant Examiner* — Marjan Fardanesh
(74) *Attorney, Agent, or Firm* — O'Shea Getz P.C.

(57) ABSTRACT

A near infrared spectrophotometric sensor assembly for non-invasive monitoring of blood oxygenation levels in a subject's body is provided. The assembly includes at least one light source, at least one light detector operable to detect light emitted by the light source, an electromagnetic interference shielding disposed around at least a portion of the light detector, wherein the electromagnetic interference shielding includes an electrically conductive substrate that is optically transparent, and one or both of a light blocking sheet disposed relative to at least one of the light detectors and an encapsulating material.

7 Claims, 7 Drawing Sheets

(56) References Cited

U.S. PATENT DOCUMENTS

| | | |
|---|---|---|
| 2004/0210263 A1 | 10/2004 | Schulman |
| 2005/0015134 A1* | 1/2005 | Carim ................. A61B 5/0408 607/142 |
| 2006/0189860 A1 | 8/2006 | Hacker et al. |
| 2007/0177075 A1* | 8/2007 | Kimoto .............. A61B 1/00048 349/110 |
| 2007/0219440 A1 | 9/2007 | Hannula et al. |
| 2008/0306357 A1 | 12/2008 | Korman |
| 2009/0108205 A1 | 4/2009 | Duffy et al. |
| 2009/0182209 A1 | 7/2009 | Benni |
| 2009/0259114 A1 | 10/2009 | Johnson et al. |
| 2010/0049018 A1 | 2/2010 | Duffy et al. |
| 2010/0102410 A1 | 4/2010 | Nakagawa et al. |
| 2010/0301215 A1* | 12/2010 | Gonopolskiy ..... A61B 5/14552 250/338.1 |

* cited by examiner

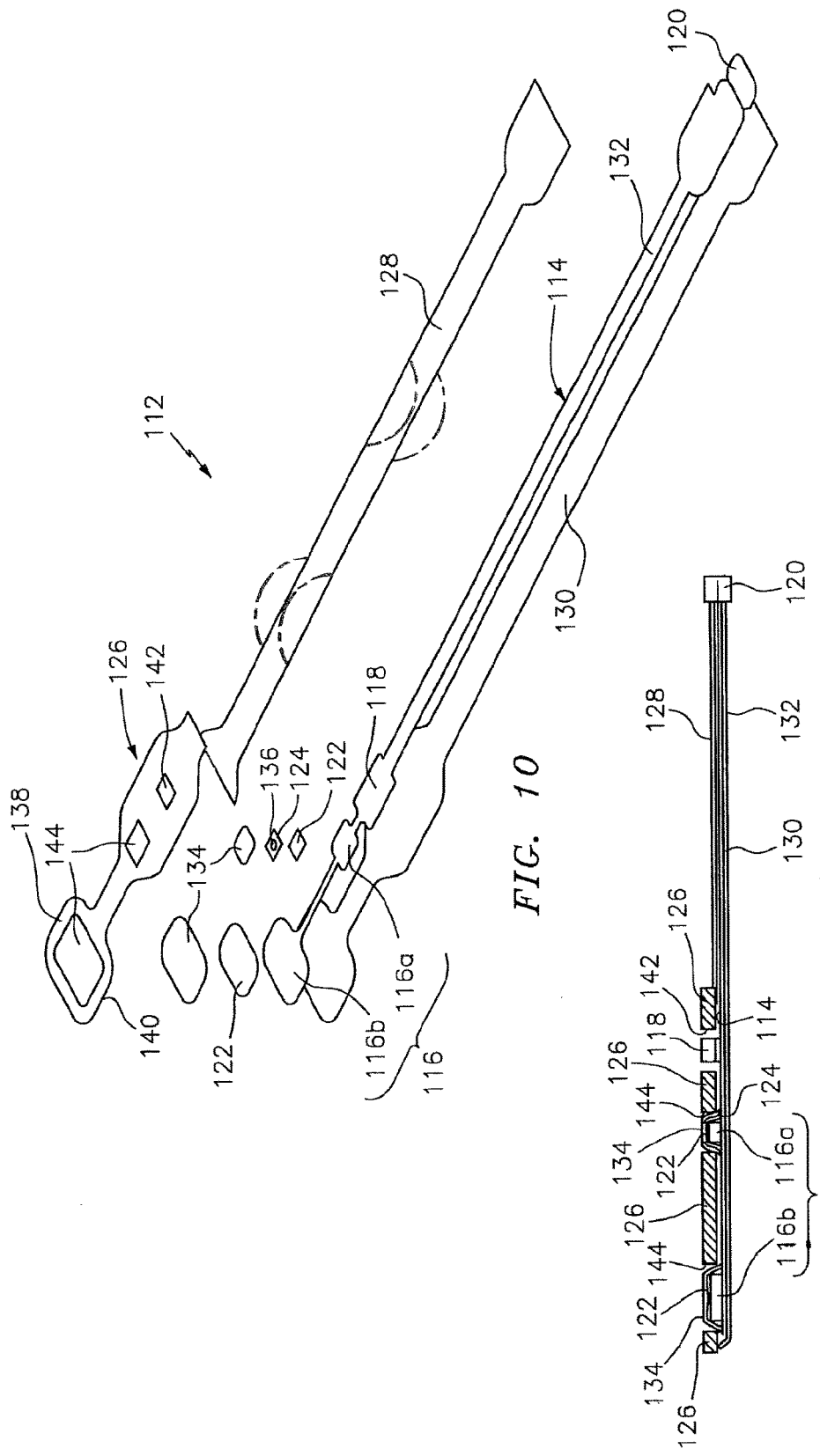

NIRS SENSOR ASSEMBLY INCLUDING ELECTRICALLY CONDUCTIVE AND OPTICALLY TRANSPARENT EMI SHIELDING

This application is entitled to the benefit of, and incorporates by reference essential subject matter disclosed in PCT Application No. PCT/US2012/024889 filed on Feb. 13, 2012, which claims priority to U.S. Provisional Patent Application No. 61/442,273 filed Feb. 13, 2011, and U.S. Provisional Patent Application No. 61/546,821 filed Oct. 13, 2011.

BACKGROUND OF THE INVENTION

1. Technical Field

This invention relates to methods and apparatus for non-invasively determining biological tissue oxygenation utilizing near-infrared spectroscopy (NIRS) techniques in general, and to sensors for use with such techniques in particular.

2. Background Information

Near-infrared spectroscopy is an optical spectrophotometric method that can be used to continuously monitor tissue oxygenation. The NIRS method is based on the principle that light in the near-infrared range (700 nm to 1,000 nm) can pass easily through skin, bone and other tissues where it encounters hemoglobin located mainly within microcirculation passages; e.g., capillaries, arterioles, and venuoles. Hemoglobin exposed to light in the near-infrared range has specific absorption spectra that varies depending on its oxidation state; i.e., oxyhemoglobin ($HbO_2$) and deoxyhemoglobin (Hb) each act as a distinct chromophore. By using light sources that transmit near-infrared light at specific different wavelengths, and measuring changes in transmitted or reflected light attenuation, concentration changes of the oxyhemoglobin ($HbO_2$) and deoxyhemoglobin (Hb) can be monitored. The ability to continually monitor cerebral oxygenation levels, for example, is particularly valuable for those patients subject to a condition in which oxygenation levels in the brain may be compromised, leading to brain damage or death.

NIRS type sensors typically include at least one light source and one or more light detectors for detecting reflected or transmitted light. The light signal is created and sensed in cooperation with a NIRS system that includes a processor and an algorithm for processing signals and the data contained therein. U.S. Pat. No. 7,047,054 and PCT International Application Serial No. PCT US0641268, which are commonly assigned with the present application to CAS Medical Systems, Inc. of Branford, Conn., disclose examples of such a sensor. Light sources such as light emitting diodes (LEDs) or laser diodes that produce light emissions in the wavelength range of 700-1000 nm are typically used. A photodiode or other light detector is used to detect light reflected from or passed through the tissue being examined. The NIRS System cooperates with the light source(s) and the light detectors to create, detect, and analyze the signals in terms of their intensity and wave properties. U.S. Pat. Nos. 6,456,862 and 7,072,701, which are commonly assigned to CAS Medical Systems, Inc., of Branford, Conn., disclose a methodology for analyzing such signals. U.S. Pat. Nos. 6,456,862 and 7,072,701, and PCT Application Serial No. PCT US0641268 are hereby incorporated by reference in their entirety.

Meaningful cerebral oxygenation information is collected from light interrogating brain tissue (e.g., passing through, reflecting from, absorbed by, etc.). To non-invasively access the brain tissue, however, the light signal must pass through extra cerebral tissue (e.g., scalp, skull, etc.) before and after interrogating the brain tissue. A light signal traveling within any biological medium (e.g., tissue, fluid, etc.) will attenuate, and the amount of attenuation is a function of the medium. In the case of a mean optical path that non-invasively accesses brain tissue, the attenuation attributable to the extra cerebral tissue does not yield useful information with respect to the cerebral oxygenation. Consequently, it is desirable to account for the signal attenuation attributable to extra cerebral tissue, so that the attenuation attributable to the brain tissue can be distinguished and analyzed.

It is known to use a NIRS sensor having a pair of light detectors specifically spaced apart from a light source as a means to account for extra cerebral tissue. A "near" light detector may be spaced apart from a light source by a first separation distance, and a "far" detector may be spaced apart from the light source by a second separation distance, which is typically greater than first separation distance. The method for spectrophotometric blood oxygenation monitoring disclosed within U.S. Pat. No. 7,072,701 is an example of a method that can be used with two detectors.

A problem common to all NIRS sensors is signal interference from electromagnetic interference (EMI) sources. Mitigating the effect of such interference improves the quality of the signal available, and therefore the patient information available. Another problem common to all NIRS sensors is the cost to manufacture. NIRS sensors are typically disposed of after use, so the cost of the sensor is an important factor in the cost of the monitoring.

What is needed, therefore, is an improved sensor for non-invasively determining the level of oxygen saturation within biological tissue, one that can be configured with one or more detectors, one that mitigates interference, and one that can be readily manufactured.

DISCLOSURE OF THE INVENTION

According to an aspect of the present invention, a NIRS sensor assembly for non-invasive monitoring of blood oxygenation levels in a subject's body is provided. The sensor assembly comprises at least one light source, at least one light detector, electromagnetic interference (EMI) shielding, and a light blocking sheet. The light source is operable to emit light signals of a plurality of different wavelengths, including those in the near-infrared range. The light detector is operable to detect light emitted by the light source and passed through the subject's body tissue. The shielding, which is disposed around at least a portion of the light detector, attenuates local EMI and thereby reduces undesirable noise within the light detector signals. The light blocking sheet is disposed relative to at least one of the light detectors, and includes an aperture sized to mate with the active area of the light detector with which it is disposed.

According to an aspect of the present invention, a NIRS sensor assembly for non-invasive monitoring of blood oxygenation levels in a subject's body is provided. The sensor assembly comprises a pad, at least one light source, at least one light detector, and electromagnetic interference (EMI) shielding. The light source is operable to emit light signals of a plurality of different wavelengths, including those in the near-infrared range. The light detector is operable to detect light emitted by the light source and passed through the subject's body tissue. The shielding, which is disposed around at least a portion of the light detector, attenuates local EMI and thereby reduces undesirable noise within the light detector signals.

According to another aspect of the present invention a near infrared spectrophotometric sensor assembly for non-invasive monitoring of blood oxygenation levels in a subject's body tissue is provided. The assembly includes a flexible circuit, at least one light detector, at least one light source, an electrical connector, EMI shielding, a light blocking sheet, and a pad. The at least one light detector is in electrical communication with the flexible circuit. The light detector has an active area for receiving light signals. The at least one light source is in electrical communication with the flexible circuit. The electrical connector is in electrical communication with the flexible circuit. The EMI shielding is disposed relative to the at least one light detector. The light blocking sheet is disposed relative to at least one of the light detectors, and includes an aperture sized to mate with the active area of the light detector with which it is disposed. The pad has a detector aperture and a light source aperture, and the pad is positioned within the assembly to contact the subject during operation of the sensor.

These and other features and advantages of the present invention will become apparent in light of the drawings and detailed description of the present invention provided below.

BRIEF DESCRIPTION OF THE DRAWINGS

FIG. 10 is an exploded view of a NIRS sensor assembly embodiment.

FIG. 11 is a sectional view of the NIRS sensor assembly embodiment shown in FIG. 10.

DETAILED DESCRIPTION OF THE INVENTION

Figure 1:
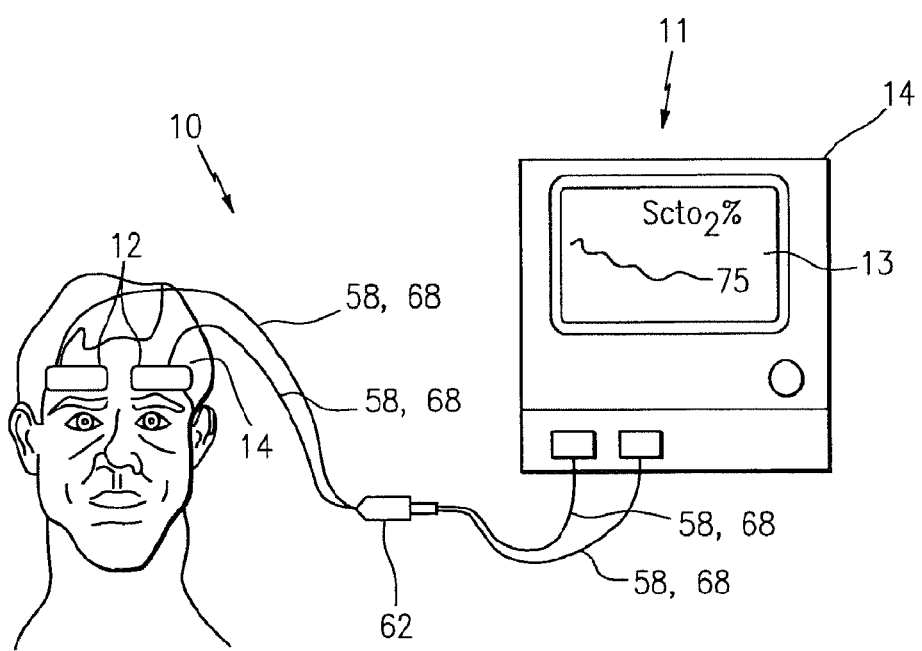
FIG. 1 is a diagrammatic view of a pair of NIRS sensor assemblies mounted on a patient and connected to a NIRS system.

Referring now to the drawings, a near infrared spectroscopy (NIRS) system 10 includes one or more NIRS sensor assemblies 12 connected to a base unit 11. The base unit 11 includes a display 13, operator controls, and a processor 14 for providing signals to and/or receiving signals from the NIRS sensor assembly(ies) 12. The processor 14 is adapted (e.g., programmed) to selectively perform the functions necessary to operate the sensor(s). It should be noted that the functionality of the processor 14 may be implemented using hardware, software, firmware, or a combination thereof. A person skilled in the art would be able to program the processor 14 to perform the functionality described herein without undue experimentation. For purposes of providing a detailed description of the present NIRS sensor assembly 12, the sensor assembly 12 will be described herein as being used in connection with the NIRS system described in U.S. Pat. Nos. 6,456,862 and 7,072,701, which are examples of acceptable NIRS systems. The NIRS sensor assembly 12 is not, however, limited to use with any particular NIRS system.

An embodiment of a NIRS sensor assembly 12 is shown in FIGS. 2-8. The NIRS sensor assembly 12 includes a pad 16, at least one light source 18, at least one light detector 20, a detector housing 22, electromagnetic interference (EMI) shielding 24, and a cover 26. In those embodiments of the present sensor assembly 12 that include more than one light detector 20, the present invention may include a plurality of detector housings 22. The present invention sensor is not limited to this particular NIRS sensor assembly, which is described herein for illustrative purposes. Specifically, the present invention includes novel, unobvious, and advantageous EMI shielding configurations (described below) that may be used with a variety of different NIRS sensors.

Figure 2:
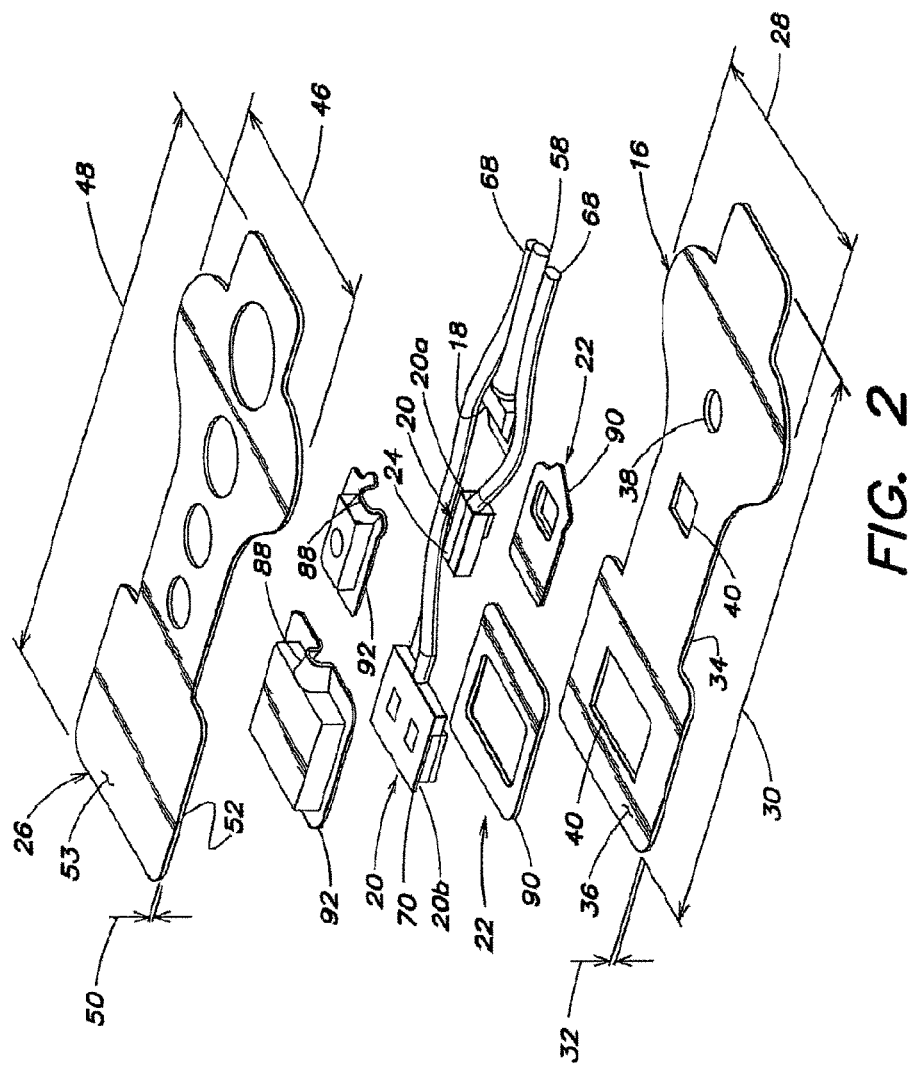
FIG. 2 is an exploded view of a NIRS sensor assembly embodiment.
Figure 3:
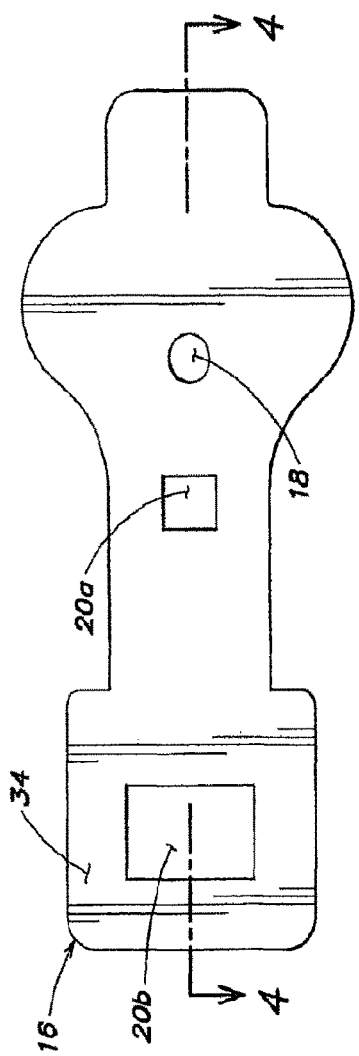
FIG. 3 is a diagrammatic planar view of a portion of the NIRS sensor assembly embodiment shown in FIG. 2, illustrating the patient side surface of the pad.
Figure 4:
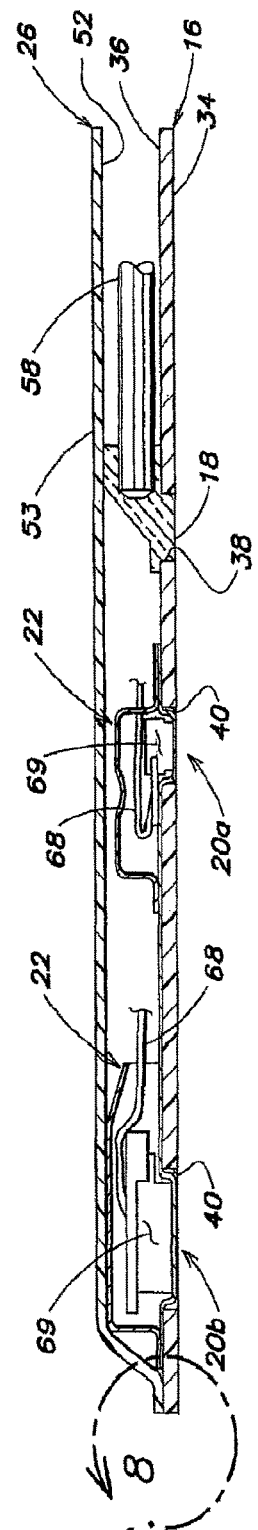
FIG. 4 is a sectional view of the NIRS sensor assembly portion shown in FIG. 3, sectioned along line 4-4.

Now referring to the embodiment shown in FIGS. 2 and 3, the pad 16 has a width 28, a length 30, a substantially uniform thickness 32, a patient side surface 34, a hardware side surface 36, at least one source aperture 38, and at least one detector aperture 40. The width 28 and length 30 are preferably contoured around one or both of the source aperture 38 and the detector aperture 40. In the embodiment shown in FIGS. 2 and 3, the pad 16 includes a pair of detector apertures 40 and a source aperture 38. The detector apertures 40 are each shaped to receive a portion of a detector housing 22, and the source aperture 38 is shaped to receive a portion of the light source 18. The detector and source apertures 40, 38 are typically aligned along a center line 42 of the pad 16. In some embodiments an adhesive 17 is applied to the patient side surface 34 for attaching the pad 16 to the patient (see FIG. 8). A removable protective layer 44 may be mounted on the adhesive covered patient side surface 34 to protect the adhesive until use. In some embodiments an adhesive is applied to the hardware side surface 36.

The pad 16 is preferably made from a flexible material (e.g., foam) that substantially or completely blocks the transmission of light energy through the pad 16. Poron® cellular urethane foam, a product of Rogers Corporation of Woodstock, Conn. USA, is an example of an acceptable pad 16 material.

In the embodiment shown in FIG. 2, the cover 26 has a geometry that matches the geometry of the pad 16. The cover 26 has a width 46, a length 48, a thickness 50, a hardware side surface 52, and an outer surface 53. The cover 26 may be made of a number of different materials, including the foam such as Poron® cellular urethane foam.

Figure 8:
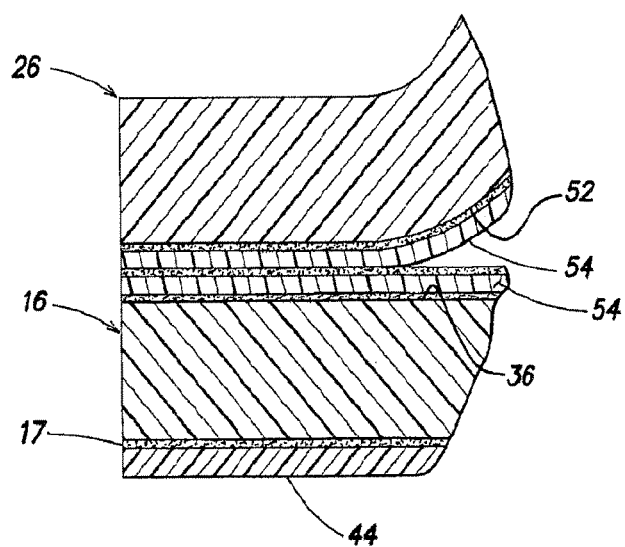
FIG. 8 is a sectional view of a portion of the sectional view shown in FIG. 4.
Figure 9:
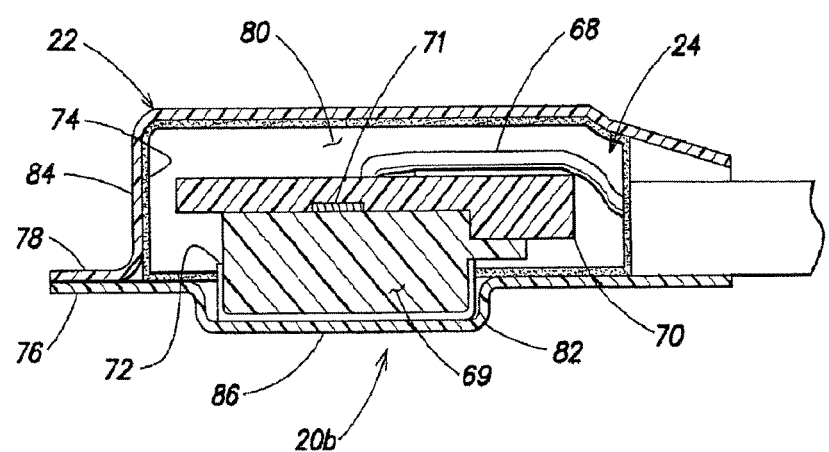
FIG. 9 is a sectional view of the detector housing shown in FIG. 4, illustrating an alternate shielding embodiment.

Referring to FIG. 8, one or more support layers 54 may be attached to one or both of the pad 16 and the cover 26. The support layer 54 is flexible, and may be described as having a width and a length oriented in similar direction as the width and length of the pad 16 and the cover 26. The support layer 54 resists stretching in the widthwise and/or lengthwise directions. Once a support layer 54 is attached to the pad 16 or to the cover 26, therefore, the support layer 54 resists stretching of the individual pad 16 or cover 26, and collectively the entire sensor assembly 12. An example of an acceptable support layer 54 material is Reemay® brand spunbonded polyester media, style no. 2006, offered by Reemay, Inc, of Charleston, S.C., USA. The present invention is not limited, however, to support layers 54 consisting of Reemay® brand spunbonded polyester media. In the embodiment shown in FIG. 8, a first support layer 54 is adhered to the hardware side surface 52 of the cover 26, and a second support layer 54 is adhered to the hardware side surface 36 of the pad 16.

The light source 18 is selectively operable to guide or emit infrared light (i.e., light in wavelength range of about 700 nm to about 1,000 nm). As stated above, infrared light provides particular utility in determining tissue oxygenation because hemoglobin exposed to light in the near-infrared range has specific absorption spectra that varies depending on its oxidation state; i.e., oxyhemoglobin ($HbO_2$) and deoxyhemoglobin (Hb) each act as a distinct chromophore. In alternative embodiments, however, there may be utility in examining blood metabolites that are best examined with a light outside the infrared range; e.g., in the visible light range between 400 nm and 700 nm, such as red light at 650 nm, or green light at 510 nm, or both visible and infrared light combinations, etc. In those applications, a light source may be utilized that emits or guides light outside the infrared range. In some embodiments, the light source 18 is an assembly that includes a fiber optic light guide 58 and a light redirecting prism 60. One end of the fiber optic guide 58 is optically connected to the prism 60. The other end of the fiber optic guide 58 is typically disposed within a connector 62 (see FIG. 1) that permits the fiber optic guide 58 to be optically coupled to fiber optic guide connected to the NIRS system 10. Other embodiments may have an optical fiber that is bent to create the proper alignment (e.g., bent ninety degrees (90°). Examples of acceptable connector 62 embodiments are disclosed below. The fiber optic light guide 58 is diagrammatically shown in FIGS. 4 and 7 as a single fiber light guide. The fiber optic light guide 58 is not limited to a single fiber embodiment, and may comprise a plurality of fibers in alternative embodiments. In alternative embodiments, the light source 18 includes one or more light emitting diodes (LEDs) mounted within the sensor assembly 12 in place of, or in combination with, the fiber optic light guide 58 and prism 60. The one or more LEDs are electrically connected to and operationally controlled by elements (e.g., processor 14) disposed within the base unit 11.

In the fiber optic light source embodiments described above, the light source 18 does not create a light signal itself. Rather, a light signal or signals (collectively referred to hereinafter as a light signal) are introduced into the fiber optic guide 58 at a position external of the NIRS sensor assembly 12, and are guided into the sensor assembly 12 via the fiber optic guide 58. The present invention NIRS sensor assembly 12 is not limited to use with any particular method and/or apparatus for introducing a light signal into the fiber optic guide 58. U.S. Pat. No. 7,047,054, incorporated by reference hereinabove, discloses an acceptable example of an apparatus for introducing light energy into the fiber optic guide 58 that includes the use of laser diodes.

A light signal exits the fiber optic guide 58 and enters the prism 60 through an entrance face 64 and is redirected out of the prism 60 through an exit face 66. The fiber optic guide 58 can be connected to the entrance face 64 of the prism 60 in a variety of different ways. For example, the fiber optic guide 58 can be butted against the entrance face 64 of the prism 60 and held in place by a layer of clear epoxy disposed between the prism 60 and the fiber optic guide 58. In some embodiments, the prism 60 may be disposed within the NIRS sensor assembly 12 so that it will contact the patient's skin during use of the NIRS sensor assembly 12. The prism 60 is rigid so that when it is pressed against the patient's skin during the monitoring of blood oxygen, the surface of the skin is flattened, and the distance between the fiber optic guide 58 output and the skin surface via the prism 60 is constant across the entire illuminated area of the skin. This configuration controls the input light intensity and light illumination spot size on the skin, which is important in making accurate measurements. In the embodiments wherein the light source 18 includes one or more LEDs mounted within the sensor assembly 12, light signals emitted from the LED(s) impinges on the subject's skin.

Figure 7:
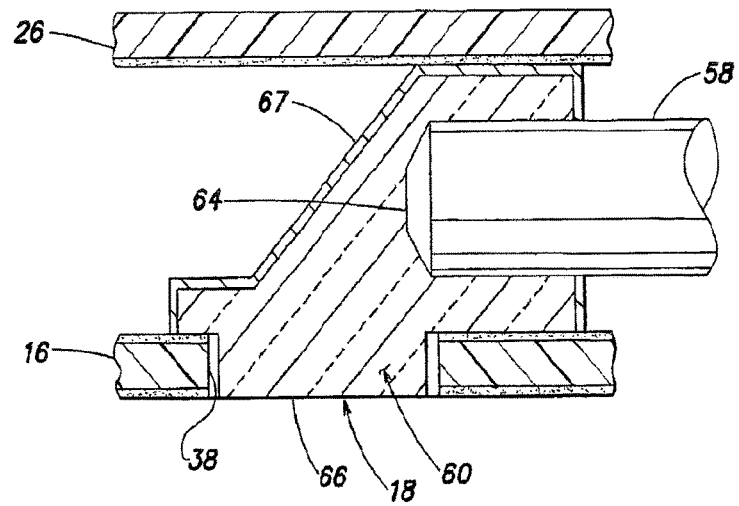
FIG. 7 is a sectional view of the light source shown in FIG. 4.

In the embodiment shown in FIG. 7, optical shielding 67 operable to at least partially impede the passage of light into or out of the prism 60 from a surface other than the entrance face 64 and exit face 66 is disposed around at least a portion of the prism 60. An example of an acceptable optical shielding 67 is a metal (e.g., copper) foil tape.

The light detector(s) 20 includes a light responsive transducer such as a photodiode that is operable to sense light intensity derived from light emitted by the light source 18 after such light passes through a portion of the subject's body. The light detectors 20 are electrically connected to the NIRS system to enable the output of the light detectors be communicated to the NIRS system 10. In a preferred embodiment, one or more EMI shielded cables 68 connect the light detectors 20 to the NIRS system 10. In the sensor embodiments having two light detectors 20, the light detector disposed closest to the light source 18 may be referred to as the "near detector 20a" and the other detector 20 disposed further away from the light source 18 as the "far detector 20b".

In the sensor embodiment shown in FIGS. 2-6, the far detector 20b includes a pair of photodiodes 69 mounted on a substrate 70 that includes a printed circuit board 71. The photodiodes 69 in the far detector 20b are electrically connected to the printed circuit board 71, and the printed circuit board, in turn, is electrically connected to the shielded cable 68. The near detector 20a includes a single photodiode 69 connected to the shielded cable 68. The number of photodiodes in one or both of the near and far detectors 20a, 20b may change to suit a particular application. In alternative embodiments, the substrate 70 may include a flexible circuit.

Figure 5:
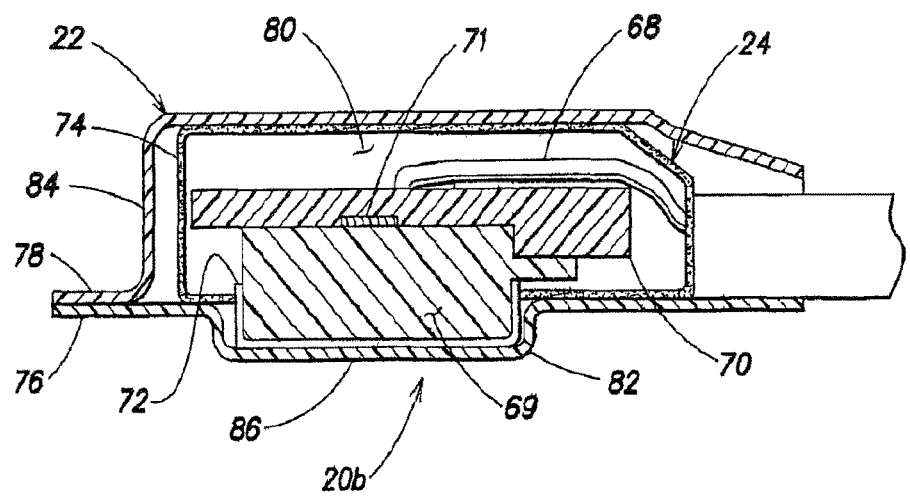
FIG. 5 is a sectional view of the detector housing shown in FIG. 4, containing the far detector.
Figure 6:
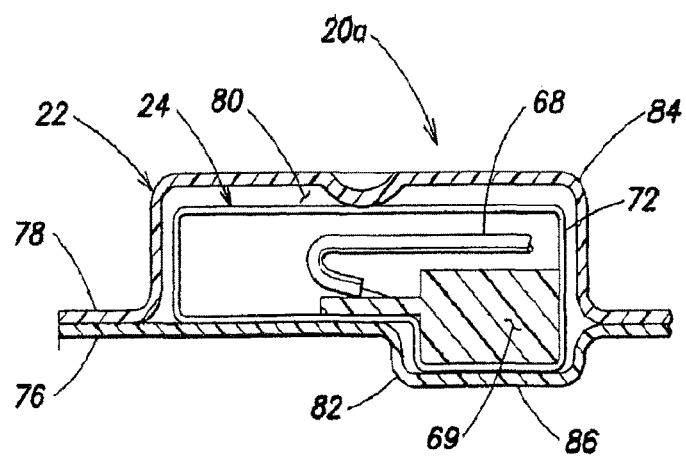
FIG. 6 is a sectional view of the detector housing shown in FIG. 4, containing the near detector.

FIGS. 5 and 6 illustrate EMI shielding 24 disposed relative to the near and far light detectors 20a, 20b. The shielding 24 embodiment for the far detector 20b shown in FIG. 5 includes an optically transparent portion 72 and a non-transparent portion 74. In this embodiment, the non-transparent portion 74 of the EMI shielding 24 is disposed around substantially the entirety of the far detector 20b, and the transparent portion 72 is disposed in alignment with the light detection surfaces of the sensor 20b. For purposes of this description, the term "optically transparent" may be defined as follows: an optically transparent medium is one through which an amount of light may pass through, which amount is adequate for purposes of a NIRS evaluation. Conversely, an "optically non-transparent" medium is one that prevents passage of substantially all of light there through, which light would otherwise be available for a NIRS evaluation. In other embodiments, the EMI shielding 24 embodiment may consist entirely of an optically transparent portion 72, or it may include portions that are less than optically non-transparent; e.g., disposed in areas outside of alignment with the light detection surfaces of the sensor 20b. The EMI shielding 24 is preferably directly or indirectly connected to ground, but not necessarily.

As indicated above, a percentage of the light signal produced by the light source 18 passes through the biological tissue of the patient, then through the optically transparent portion 72 of the EMI shielding 24, after which it is sensed by the far light detector 20b. At the same time, the optically transparent portion 72 attenuates local EMI that may be present.

In some embodiments, the optically transparent portion 72 includes a structure that is operable to isotropically distribute EMI. For example, the optically transparent portion 72 may include an electrically conductive wire mesh (e.g., copper wire mesh). As another example, the optically transparent portion 72 may include a thin electrically conductive substrate that is optically transparent as described above. An example of such an electrically conductive substrate is a fiber-filled, conductive adhesive tape such as XYZ-Axis Electrically Conductive Tape 9713, offered by 3M Company of St. Paul, Minn., USA. The electrically conductive substrate (e.g., 9713 Tape) may contain electrically conductive fibers that allow for isotropic distribution of EMI. The electrically conductive substrate can come in a double sided form that has adhesive on both sides. An electrically conductive substrate (e.g., the 9713 Tape) provides several advantages, including: (1) it is relatively inexpensive; (2) it does not require a soldered connection to ground; (3) it is available in roll form; (4) it has a low profile; and (5) it is flexible. In embodiments in which the sensor includes a flexible circuit, use of an electrically conductive substrate like the 9713 Tape on, in, or around the flexible circuit is particularly advantageous because the electrically conductive substrate in combination with the flexible circuit can improve the flexibility of the sensor while still providing adequate EMI shielding for the sensor. The ability to utilize the electrically conductive substrate on, in, or around the flexible circuit provides considerable utility. The present invention is not limited to using 9713 Tape as an electrically conductive substrate that is optically transparent, and other similar products may be used alternatively.

In those embodiments of the EMI shielding 24 that utilize an optically non-transparent portion 74, that portion 74 may include an electrically conductive metal foil, such as a copper metal foil. In those embodiments in which the optically transparent portion 72 includes an electrically conductive substrate like the 9713 Tape, the non-transparent portion 74 may be adhered to the transparent portion 72 in those areas of the detector 20a, 20b not utilized to sense light. An electrically conductive gasket, such as silicone paste, adhesive, foam, or other similar material, may be used to create an electrical interface between the optically transparent and optically non-transparent portions 72, 74 of the shielding 24, particularly in those embodiments that utilize a wire mesh as the optically transparent portion 72.

The EMI shielding 24 for the near detector 20a includes an arrangement similar to those described above for the far detector 20b. The EMI shielding embodiment used on the near detector 20a may be different from that used on the far detector 20b. For example, in the embodiment shown in FIG. 6, optically transparent shielding 24 is disposed around substantially the entirety of the near light detector 20a.

The above-described shielding 24 reduces undesirable EMI generated noise, and improves the signal to noise ratio of the light detectors 20 (e.g., photodiodes). For example, the optically transparent shielding 24 creates a Faraday Cage around the light detector 20, while allowing light to reach the light-sensitive surface of the light detector 20. In fact, the EMI shielding of the present invention can be implemented to create as few as one Faraday Cage operable to provide the requisite EMI shielding, or alternatively can be implemented to create more than one Faraday Cage relative to the sensor to provide the requisite EMI shielding. For example, in one embodiment, a detector 20 may be protected from interference by creating two Faraday Cages; e.g., a first Faraday cage surrounding the electronic circuitry of the sensor and a second Faraday Cage around the light detector 20 itself. The present invention is not limited to any particular Faraday Cage embodiment. In those instances where the present invention shielding 24 is used within the exemplary sensor embodiment described herein, the detector housings 22 also create further EMI attenuation by increasing the light detector-to-biological tissue separation distance. The optically transparent spacer created by the detector housing 22 reduces the capacitance between the light detector 20 light sensitive surface and the biological tissue, such as human skin, resulting in an increased reduction in electromagnetic coupling and generated noise currents when compared to a sensor application that does not include such an optical spacer.

In those sensor embodiments that utilize a detector housing 22, the detector housing 22 includes a base 76 and a cap 78 that together define an internal cavity 80, which cavity 80 is sized to enclose a light detector 20 at least partially covered with shielding 24 (and other materials as applicable). The base 76 and the cap 78 may be hinged together or they may be separable. The cap 78 includes a port 88 (see FIG. 2) for receiving a shielded cable 68. Alternatively, the port 88 may be partially disposed in both the base 76 and the cap 78, or solely in the base 76. The base 76 includes a well 82 sized to receive at least a portion of the light detector 20, and the cap 78 is sized to receive the remainder of the light detector 20 not received within the base well 82. The detector housing embodiments shown in FIGS. 2-6, for example, include a base 76 having a well 82 and a cap 78 having a well 84, which wells 82, 84 are sized to receive the light detector 20 in combination. In other embodiments, the base well 82 may be sized to receive the entire light detector 20 and shielding 24, and the cap 78 may be planar across the base well 82, or shaped to extend into the base well 82.

In some embodiments, the dimensions of the internal cavity 80 (i.e., height, width, depth) are such that there is a slight press fit between the light detector 20, shielding 24, etc. and the housing 22. As a result, the light detector 20 is positionally located and maintained within the housing 22. In alternative embodiments, the light detector 20 and shielding 24 may be positionally located and maintained within the internal cavity 80 by features (e.g., stems, ribs, etc.) integrally formed with the base 76 or cap 78, or elements disposed within the internal cavity 80 (e.g., a spacer, or biasing element), or by other means.

The base well 82 includes a window panel 86 that consists of an optically transparent material that allows light to pass there through and be sensed by the light detector 20. The window panel 86 may be an optically flat surface or it may be modified to focus or defocus detected light. The window panel 86 may also be treated to act as a filter with respect to chromaticity, wavelength, etc.

The base 76 and the cap 78 may be made out of the same material or different materials. In a preferred embodiment, the base 76 and cap 78 are formed from a material that has favorable dielectric characteristics (e.g., electrically insulative). The particular material, and therefore the dielectric characteristics, can be chosen to suit the application at hand. In addition, the amount of dielectric strength can also be chosen to affect the capacitance of a fixed geometry capacitor such as the window panel 86. As indicated above, the window panel 86 portion of the detector housing 22 increases the light detector-to-biological tissue separation distance, thereby reducing the capacitance between the light detector light sensitive surface and the biological tissue.

The base 76 and cap 78 engage and may attach to one another using adhesives, mechanical features (e.g., mating male/female pairs), welding, or the like. In the embodiment shown in FIGS. 2-6, the base 76 and cap 78 include mating flanges 90, 92 that attach to one another by an adhesive disposed on one or both of the flanges 90, 92. Each detector housing 22 is positioned so that at least a portion of the base well 82 is received within the respective detector aperture 40 of the pad 16. In the embodiment shown in FIGS. 2-6, the near light detector 20a and far light detector 20b are disposed within independent detector housings 22. In alternative embodiments, the bases 76 of the detector housings 22 may be connected to one another and/or the caps 78 of the detector housings 22 may be connected to one another.

The spacing between and the relative positioning of the near light detector 20a and the far light detector 20b within the sensor assembly 12 is preferably chosen so that: 1) the light source 18, near light detector 20a and the far light detector 20b are substantially linearly aligned with one another; and 2) the separation distance between the far light detector 20b and the near light detector 20a is greater than the separation distance between the light source 18 and the near light detector 20a. A greater distance between the near light detector 20a and the far light detector 20b (as compared to the separation distance between the light source 18 and the near light detector 20a) creates a significant difference between the region defined by the mean optical path extending between the light source 18 and near light detector 20a, and the region defined by the mean optical path extending between the light source 18 and the far light detector 20b. As a result, the information representing the contrast of the two signals is greater than it would be if the two mean optical paths were closer to one another.

The following examples illustrate light source 18/light detector 20 spacing for neonate, small adult/pediatric, and adult embodiments of the present sensor assembly 12. In an adult NIRS sensor assembly 12, the light source 18 may be positioned in the range of approximately forty-seven to fifty millimeters (47 mm to 50 mm) from the far light detector 20b and approximately fifteen millimeters (15 mm) from the near light detector 20a. In a small adult/pediatric embodiment of the NIRS sensor assembly 12, the light source 18 may be positioned in the range of approximately forty to forty-three millimeters (40 mm to 43 mm) from the far light detector 20b and approximately twelve millimeters (12 mm) from the near light detector 20a. In a neonate embodiment of the NIRS sensor assembly 12, the light source 18 is positioned in the range of approximately twenty-five to thirty millimeters (25 mm to 30 mm) from the far light detector 20b and approximately ten millimeters (10 mm) from the near light detector 20a. In an alternative neonate embodiment of the NIRS sensor assembly 12, the light source 18 may be positioned in the range of approximately twenty-five to thirty millimeters (25 mm to 30 mm) from a single light detector 20. The light source 18/detector 20 spacings described above represent examples and the present invention should not be construed to be limited to these examples.

In some embodiments, an EMI shielding material may be applied directly to the interior and/or exterior surfaces of the detector housing walls (e.g., wells, etc.) in addition to or in place of the EMI shielding 24 that is disposed around the light detectors 20. The EMI shielding may be applied to only some detector wall surface, or a sufficient amount of detector wall surface so as to create a Faraday Cage around the light detector 20 disposed within the housing. The shielding applied to the detector housing walls may include any of the materials (e.g., electrically conductive wire mesh, electrically conductive substrate, etc.) discussed above with regard to the EMI shielding 24 that is disposed around the light detectors 20. The shielding may be applied by processes including printing, adhering, spraying, etc.

The cover 26 is shaped and positioned on the NIRS sensor assembly 12 so that the light source 18, the detector housings 22 containing the near and far light detectors 20a, 20b, and the shielded cable 68 are disposed between the cover 26 and the pad 16. The cover 26 preferably consists of a soft pliable material that can be used in a patient environment. Examples of acceptable cover materials include, but are not limited to, vinyl materials, plastic materials and foam materials (e.g., Poron®). The cover 26 may be attached to the NIRS sensor assembly 12 in a variety of different ways; e.g., by adhesive, mechanical features, etc. The cover 26 material preferably blocks light from entering the NIRS sensor assembly 12. The cover 26 may be molded, cast or formed in place over the sensor elements to create a tailored fit.

In preferred embodiments, the NIRS sensor assembly 12 includes a connector 62 that allows for attachment and removal of the sensor assembly 12 from the NIRS system 10. The connector 62 includes a fiber optic coupler and a shielded cable coupler. The fiber optic coupler provides an interface for optically connecting the fiber optics of the NIRS sensor assembly 12 to the NIRS system 10. Similarly, the shielded cable coupler provides an interface for connecting the photodiode output of the NIRS sensor assembly 12 to the NIRS system 10. In some embodiments, the connector 62 is a hybrid connector that incorporates the fiber optic coupler and the shielded cable coupler together into a single unit. In other embodiments, the connector 62 includes a fiber optic coupler and a shielded cable coupler that are independent of one another. In those embodiments where the fiber optic coupler and the shielded cable coupler are independent of one another, the two couplers may be located apart from one another; e.g., the fiber optic coupler at the sensor and the shielded cable coupler at a mid point.

In some embodiments, a multi-fiber optic combiner may be used that allows for multiple laser light sources 18 of different wavelengths to be coupled into a small diameter core fiber optic output leading to the NIRS sensor assembly 12. The present invention sensor assembly 12 does not require the use of a multi-fiber optic coupler, and if one is used the present NIRS sensor assembly 12 is not limited to using any particular type or make of multi-fiber optic coupler. U.S. Pat. No. 7,047,054, which was earlier incorporated by reference into the present application, discloses an example of an acceptable multi-fiber optic coupler.

The connector 62 can also include sensor identification encoding means so that the NIRS system 10 can identify the type of NIRS sensor assembly 12 connected; i.e., an adult, pediatric, neonate, and other configured sensor. Once the type of sensor 12 is identified, the NIRS system 10 can then select appropriate information for use with that sensor 12; e.g., calibration information for a specific sensor configuration. Methods of encoding include but are not limited to: 1) setting different resistor values for each differently configured sensor 12 in which the NIRS system 10 can measure the resistance value though a voltage divider circuit; 2) incorporating a small memory device, such as a serial PROM, which has sensor identification information stored to be read by the NIRS system 10; and 3) including an RF identification device.

According to another aspect of the present invention, a NIRS sensor assembly 112 as shown in FIGS. 10 and 11 may be used with a NIRS system 10. The NIRS sensor assembly 112 may include some or all of the following elements: a flexible electrical circuit 114, at least one light detector 116, at least one light source 118, a connector 120, EMI shielding 122, a light blocking sheet 124, a pad 126, a bottom housing 128, and a top housing 130.

Each light detector 116 includes a light responsive transducer (e.g., a photodiode) that is operable to sense the intensity of light emitted by the light source 118 after such light passes through a portion of the subject's body. Each light detector 116 includes an active region through which impinging light can be sensed. The light detectors 116 are electrically connected to the NIRS base unit 11 to enable processing of the output of the light detectors 116. In a preferred embodiment, the light detectors 116 are mounted on a flexible electrical circuit 114 (as will be described below), which circuit provides the electrical connections between the detectors 116 and the base unit 11. In the sensor embodiments having two or more light detectors 116 spaced apart from one another and light source 118, the light detectors may be referred to as a "near detector 116a" and a "far detector 116b" (relative to the light source 118) as described above.

The light source 118 is selectively operable to produce infrared light (i.e., light in wavelength range of about 700 nm to about 1,000 nm), and in some embodiments may also produce light in the visible range. In preferred embodiments, the light source 118 is an assembly that includes a plurality of light-emitting diodes (LEDs), each selected to produce light at a predetermined wavelength. The present invention NIRS sensor assembly 112 is not limited to use with LEDs, however. As will be described below, the light source 118 is preferably mounted on a flexible electrical circuit 114 for electrical communication with the NIRS base unit 11.

The detector(s) 116 and the light source 118 are preferably mounted on a flexible electrical circuit 114 (i.e., a "flex circuit"). The flex circuit 114 may be described as a patterned arrangement of printed wiring (i.e., electrically conductive paths that may, for example, be formed by printing or etching conductive material) mounted relative to a flexible base material. The wiring of the flex circuit 114 electrically connects the detectors 116 and the light source 118 to the connector 120. The connector 120, in turn, provides the structure that allows the sensor assembly 112 to be electrically connected to the base unit 11; e.g., in signal communication with the base unit 11. In the embodiment shown in FIGS. 10 and 11, the flex circuit 114 is configured so the far detector 116b is positioned proximate one end of the flex circuit 114, and the near detector 116a is spaced apart from the far detector 116b and is disposed between the far detector 116b and the light source 118. Adjacent the light source 118, a lead portion 132 of the flex circuit 114 extends outwardly, terminating at the connector 120. Examples of acceptable configurations of the relative positioning of the detectors 116 and the light source 118 are described above; e.g., the light source 118 may be positioned approximately forty to forty-three millimeters (40 mm to 43 mm) from the far light detector 116b and approximately twelve millimeters (12 mm) from the near light detector 116a. The sensor assembly 112 is not limited to any particular detector/light source 118 spacing configuration, however.

In the embodiment shown in FIGS. 10 and 11, an encapsulation material 134 is disposed in contact with each detector 116. The encapsulation material 134 encapsulates and protects the detector 116, and the connection between the detector 116 and the flex circuit 114. The encapsulating material also provides a dielectric barrier between the patient and the electrical circuit of the sensor. In preferred embodiments, the encapsulating material also encapsulates one or both of the EMI shielding 122 and light blocking sheet 124 proximate the respective detector 116. The encapsulating material 134 also acts as an optical interface between the detector 116 and the subject (when mounted on a subject), and depending upon the type of encapsulating material 134 used, can also be operable to electrically insulate the subject from the detector 116 and the flex circuit 114. An example of an encapsulating material 134 is an ultraviolet curable epoxy; e.g., 3525 epoxy made by Loctite or a dielectric film such as FEP tape made by Dupont. In some sensor applications, it may be desirable to use encapsulating material 134 relative to only one detector 116, or not at all.

The sensor assembly 112 includes EMI shielding 122 disposed relative to the light detectors 116. An optically transparent portion of the EMI shielding 122 is disposed in alignment with the active regions of the light detectors 116. The EMI shielding 122 may also include a portion disposed around the periphery of one or more of the detectors 116, and that portion may or may not be optically transparent. For purposes of this description, the term "optically transparent" may be defined as follows: an optically transparent medium is one through which an amount of light may pass through, which amount is adequate for purposes of a NIRS evaluation under normal operating circumstances for the sensor assembly. The EMI shielding 122 is preferably directly or indirectly connected to ground, but not necessarily.

As described above, the optically transparent portion of the EMI shielding 122 may comprise an electrically conductive wire mesh (e.g., copper wire mesh) or it may comprise a thin electrically conductive substrate such as a fiber-filled, conductive adhesive tape; e.g., XYZ-Axis Electrically Conductive Tape 9713 ("9713 Tape"), offered by 3M Company of St. Paul, Minn., USA. The present invention is not limited to using 9713 Tape as an electrically conductive substrate that is optically transparent, and other similar products may be used alternatively. For those embodiments that utilize non-transparent portions of the EMI shielding 122, those portions may include an electrically conductive metal foil, such as a copper metal foil. The EMI shielding 122 may be integrated into the encapsulating material 134, or attached to an exposed surface of the encapsulating material 134. A significant advantage of the fiber-filled, conductive adhesive tape is that it can be adhered in place during assembly, which greatly facilitates assembly.

The sensor assembly 112 may further include a light blocking sheet 124 positioned below, or, on top of the encapsulating material 134 and the EMI shielding 122. The light blocking sheet 124 includes an aperture 136 sized to mate with the active region of the detector 116 with which it is positioned. In the embodiment shown in FIGS. 10 and 11, a light blocking sheet 124 is positioned relative to the near detector 116a. In alternative embodiments, the light blocking sheet 124 may be disposed relative to either the near or far detector, or both. A preferred embodiment of the light blocking sheet 124 is a thin flexible black material that has an adhesive backing that facilitates positioning and securing of the sheet 124 relative to the detector 116. A particularly useful light blocking sheet 124 is one that is also electrically conductive. An example of an acceptable light blocking sheet 124 is an electrically conductive transfer tape, model ARcare® 90366, manufactured by Adhesives Research, Inc. of Glen Rock, Pa., U.S.A. The light blocking sheet 124 is not limited to this specific product, however. For those embodiments that utilize an electrically conductive light blocking sheet 124, the conductive property of the light blocking sheet 124 facilitates the effectiveness of the EMI shielding 122. A significant advantage of adhesive backed light blocking sheet 124 is that it can be adhered in place during assembly, which greatly facilitates assembly.

The above-described structure (e.g., the stack up of flex circuit 114 and detector 116, encapsulating material, EMI shielding 122, and light blocking sheet 124) provides a structure that allows light signals to be sensed, and at the same time reduces undesirable EMI generated noise and improves the signal to noise ratio of the light detectors 116. The optically transparent shielding 122 may be described as providing a Faraday Cage around the light detector 116, while allowing light to reach the light-sensitive surface of the light detector 116. By reducing the aperture for the photodetector, light shunting from the emitter through the tissue is reduced and the path length for the transmitted light is refined.

The pad 126 has a patient side surface 138, a component side surface 140, at least one source aperture 142, and at least one detector aperture 144. Each detector aperture 144 is shaped to surround the respective detector 116, and the light source aperture 142 is shaped to surround the light source 118. In some embodiments an adhesive is applied to the patient side surface 138 for attaching the pad 126 to the subject. The pad 126 is preferably comprises a material such as that described above (e.g., Poron® cellular urethane foam).

The bottom housing 128 is disposed on the side of the sensor assembly 112 that is placed in contact with the subject. The top housing 130 is positioned on the opposite side of the sensor assembly 112. Both housings 128, 130 are preferably flexible and operable to protect the flex circuit 114 disposed between the housings 128, 130. The housings 128, 130 are attached to one another to enclose a portion of the flex circuit 114. A portion of the top housing 130 is attached to the pad 126 to enclose the portion of the sensor assembly 112 containing the detectors 116 and the light source 118. The housings 128, 130 may be made of a number of different materials, including the foam such as Poron® cellular urethane foam. In preferred embodiments, the housings comprise a synthetic material consisting of high-density polyethylene fibers which is tear resistant, but breathable (e.g., water vapor permeable). Tyvek® brand material, produced by the DuPont company, is an example of a synthetic material consisting of high-density polyethylene fibers that can be used for the housings 128, 130. The bottom housing 128 is not adhered to the component side surface 140 of the pad 126, creating a tab. The tab better adheres the sensor assembly 112 to the skin of the patient.

The connector 120 is configured to provide electrical/signal communication directly, or indirectly, between the sensor assembly 112 and the base unit 11. In some NIRS systems 10, a base unit cable extends out from the base unit 11 for connection with the sensor assembly 112. The base unit cable may include a photodiode preamplifier operable to amplify the signals from the sensor assembly 112. In the embodiment shown in FIGS. 10 and 11, the connector 120 includes a printed circuit board card ("PCB card") that mates with the base unit cable to form a shielded connection; e.g., a Hirose model LX40-16P, display port, or minidisplay port. The connector 120 is not, however, limited to a PCB card, however. An example of an alternative type of connector 120 is an I/O connector. An alternate embodiment for the sensor incorporates a cable extension that is attached between the flex circuit tail and the PCB card or I/O connector. This construction allows the sensor connector to be located remotely from the patient. The sensor assembly embodiment shown in FIGS. 10 and 11 shows the sensor 112 extending along a substantially straight line between the detector/emitter region and the connector 120. The present sensor is not limited to a straight configuration. In alternative embodiments, the region shown as straight can include one or more deviations (e.g., bends, or jogs—shown in phantom) that facilitate flexing of that portion of the sensor assembly. The additional flexibility helps to prevent inadvertent detachment of the sensor from the subject during operation of the sensor.

In the operation of the present invention, once the NIRS sensor assembly 12, 112 is positioned relative to the subject's skin, the sensor may be actuated and near infrared light signals introduced into the subject's body tissue. The light introduced into the subject's body tissue is subsequently detected using the near and far light detectors, producing signals representative of such detected light. The signals are relayed back to the NIRS base unit 11, where they are processed to obtain data relating to the blood oxygenation level of the subject's body tissue. As stated above, the present invention NIRS sensor assemblies described above are not limited to use with any particular NIRS system 10.

Since many changes and variations of the disclosed embodiment of the invention may be made without departing from the inventive concept, it is not intended to limit the invention otherwise than as required by the appended claims. For example, the present invention is disclosed in the context of a cerebral application. The present invention is not limited to cerebral oximetry applications and can be used for non-invasive monitoring of blood oxygenation levels in other body tissues and fluids.

What is claimed is:

1. A NIRS sensor assembly for non-invasive monitoring of blood oxygenation levels in a subject's body, the assembly comprising:
    at least one light source operable to emit light signals of a plurality of different wavelengths;
    at least one light detector operable to detect light emitted by the light source and passed through the subject's body tissue, which at least one light detector has an active area through which light signals may be detected;
    electromagnetic interference shielding disposed around at least a portion of the at least one light detector, wherein the electromagnetic interference shielding includes an electrically conductive substrate that is optically transparent, which optically transparent substrate is aligned with the active area of the at least one light detector;
    a flexible circuit in electrical communication with the at least one light source and the at least one light detector; and
    an encapsulation material that is disposed in contact with the at least one light detector and covers the at least one light detector and a connection between the at least one light detector and the flexible circuit, and contacts the flexible circuit, and the electromagnetic interference shielding is encapsulated by the encapsulation material.

2. The NIRS sensor assembly of claim 1, further comprising an electrical connector attached to the flexible circuit.

3. The NIRS sensor assembly of claim 2, wherein the electrical connector comprises a printed circuit board ("PCB") card.

4. The NIRS sensor assembly of claim 1, wherein the encapsulation material is an epoxy configured to provide a dielectric barrier between the subject and the flexible circuit.

5. The NIRS sensor assembly of claim 4, wherein the electromagnetic interference shielding includes one or both of an electrically conductive wire mesh and a thin electrically conductive substrate, either of which are optically transparent.

6. The NIRS sensor assembly of claim 5, wherein the thin electrically conductive substrate includes a fiber-filled, conductive adhesive tape.

7. The NIRS sensor assembly of claim 1, wherein the electromagnetic interference shielding includes a fiber-filled, electrically conductive substrate.

* * * * *